United States Patent [19]

Diana

[11] 4,182,759

[45] Jan. 8, 1980

[54] ARYLALKYL AND ARYLOXYALKYL PHOSPHONATES AND USE AS ANTIVIRAL AGENTS

[75] Inventor: Guy D. Diana, Stephentown, N.Y.

[73] Assignee: Sterling Drug Inc., New York, N.Y.

[21] Appl. No.: 912,502

[22] Filed: Jun. 5, 1978

[51] Int. Cl.$^2$ ............................ A01N 9/36; C07F 9/40
[52] U.S. Cl. ..................................... 424/217; 260/941; 260/951; 260/952; 424/212
[58] Field of Search .................. 260/951, 952, 941; 424/217, 212

[56] References Cited

U.S. PATENT DOCUMENTS

| 2,934,507 | 4/1960 | Chadwick et al. | 260/951 |
| 3,917,718 | 11/1975 | Collins | 260/613 R |
| 4,031,246 | 6/1977 | Collins et al. | 424/331 |

OTHER PUBLICATIONS

Baron et al., "Annual Reports in Medicinal Chemistry", Chapter on Antiviral Agents, vol. 10, (1970), p. 166.
Linn et al., "J. Am. Chem. Soc.", vol. 87 (1965), pp. 3657–3672.

*Primary Examiner*—Anton H. Sutto
*Attorney, Agent, or Firm*—Thomas L. Johnson; B. Woodrow Wyatt

[57] ABSTRACT

Arylalkyl and aryloxyalkylphosphonates, useful as antiviral agents, are prepared by reacting an arylalkyl or aryloxyalkyl halide with a trialkyl phosphite, or with an alkali metal salt of a dialkyl phosphonate, trialkyl phosphonoalkanoate or dialkyl phosphonoalkanone.

15 Claims, No Drawings

ARYLALKYL AND ARYLOXYALKYL PHOSPHONATES AND USE AS ANTIVIRAL AGENTS

BACKGROUND OF THE INVENTION (a) Field of the Invention

The invention relates to arylalkyl- and aryloxyalkyl-phosphonates, to the preparation thereof, and to compositions and methods for the use thereof as antiviral agents.

(b) Description of the Prior Art

J. C. Collins U.S. Pat. No. 3,917,718, issued Nov. 4, 1975, discloses compounds useful as pesticidal and antiviral agents and having the formula

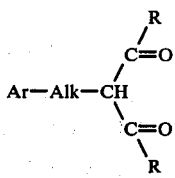

wherein Ar is phenyl or substituted phenyl, Alk is alkylene of 6-10 carbon atoms, and R is lower-alkyl. The compounds are prepared by reacting an arylalkyl halide, Ar-Alk-X, where X is bromine or iodine with an alkali metal salt of a diketone having the formula $H_2C(COR)_2$.

J. C. Collins and G. D. Diana U.S. Pat. No. 4,031,246, issued June 21, 1977, discloses compounds useful as pesticidal and antiviral agents and having the formula

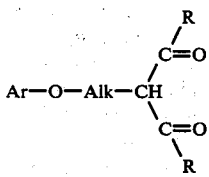

wherein Ar is phenyl or substituted phenyl, Alk is alkylene of 3-10 carbon atoms and R is lower-alkyl. The compounds are prepared by reacting an aryloxyalkyl halide, Ar-O-Alk-X, where X is bromine or iodine with an alkali metal salt of a diketone of the formula $H_2C(COR)_2$.

Sodium phosphonoacetate, $(HO)_2P(O)CH_2COONa$, has shown antiviral activity against herpes infections in test animals; cf. S. Baron and G. Galasso, Chapter on Antiviral Agents, page 166, Annual Reports in Medicinal Chemistry, Vol. 10 (1975).

W. J. Linn and R. E. Bensen, J. Am. Chem. Soc. 87, 3657-72 (1965), at page 3671 disclose the compound diethyl (4-methylbenzyl)phosphonate, 4-$CH_3C_6H_4CH_2P(O)(OC_2H_5)_2$, as a chemical intermediate.

SUMMARY OF THE INVENTION

In a composition of matter aspect, the invention relates to compounds having the formula

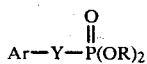

wherein

Ar is phenyl or phenyl substituted by one or two substituents selected from the group consisting of halogen, lower-alkoxy of 1 to 4 carbon atoms, hydroxy, alkanoyloxy of 1-4 carbon atoms, carbo-lower-alkoxy of 2-4 carbon atoms, carbamyl and carboxy;

Y is $(CH_2)_n$ or $O(CH_2)_n$ wherein n is an integer from 6 to 8; and R is alkyl of 1-6 carbon atoms.

In a further composition of matter aspect, the invention relates to compounds having the formula

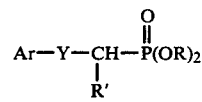

wherein

Ar is phenyl or phenyl substituted by one or two substituents selected from the group consisting of halogen, lower-alkoxy of 1 to 4 carbon atoms, hydroxy, alkanoyloxy of 1-4 carbon atoms, carbo-lower-alkoxy of 2-4 carbon atoms, carbamyl and carboxy;

Y is $(CH_2)_m$ or $O(CH_2)_m$ where m is an integer from 3 to 10;

R is alkyl of 1-6 carbon atoms;

and R' is alkanoyl or carboalkoxy of from 2 to 4 carbon atoms.

In a further composition of matter aspect, the invention relates to a composition for combatting viruses which comprises an antivirally effective amount of a compound of Formula I or II in admixture with a suitable carrier or diluent.

In a process aspect, the invention relates to a process for preparing a compound of Formula I which comprises heating a compound having the formula Ar-Y-X, where X is bromine or iodine, with a compound having the formula $P(OR)_3$ or an alkali metal salt of a compound having the formula $HP(O)(OR)_2$.

In a further process aspect, the invention relates to a process for preparing a compound of Formula II which comprises heating a compound having the formula Ar-Y-X, where X is bromine or iodine, with an alkali metal salt of a compound having the formula $R'CH_2-P(O)(OR)_2$.

In a further process aspect, the invention relates to a method of combatting viruses which comprises contacting the locus of said viruses with an antivirally effective amount of at least one compound of Formula I or II.

DETAILED DESCRIPTION INCLUSIVE OF PREFERRED EMBODIMENTS

The compounds of Formula I are prepared by either of two alternative methods, both starting from a common intermediate halide having the formula Ar-Y-X.

In the first method, the arylalkyl or aryloxyalkyl halide is heated with a trialkyl phosphite, $P(OR)_3$, preferably at a temperature between about 150° and 200° C. The relatively volatile alkyl halide, RX, is formed and distilled out of the reaction mixture leaving behind the product of Formula I which can be purified by distillation at reduced pressure or chromatographic procedures.

In the second method, the arylakyl or aryloxyalkyl halide is heated with the alkali metal salt of a dialkyl phosphonate, $HP(O)(OR)_2$, said alkali metal salt being prepared in situ from the phosphonate and an alkali metal, preferably sodium or potassium, in an inert organic solvent prior to addition of the halide. The reaction occurs readily at a temperature between about 50° and 100° C., conveniently at the reflux temperature of the inert solvent, for example, hexane or tetrahydrofuran. In the event the arylalkyl halide or aryloxyalkyl halide is a bromide, the reaction can be catalyzed by the addition of a trace of iodine or sodium iodide.

The intermediate arylakyl halides and aryloxyalkyl halides, Ar-Y-X, are a known class of compounds, described in Collins U.S. Pat. No. 3,917,718 and Collins and Diana U.S. Pat. No. 4,031,246, respectively.

The compounds of Formula II are prepared by a process analogous to the second method for preparing the compounds of Formula I, that is, by reacting an arylalkyl halide or aryloxyalkyl halide, Ar-Y-X, with a compound having the formula R'CH$_2$P(O)(OR)$_2$ in the presence of a strong base, such as an alkali metal, e.g. lithium, sodium or potassium, or a strong base derived therefrom, e.g. a hydride or amide, which forms the alkali metal salt of the phosphonate involving the active methylene group (CH$_2$) intervening between the carbonyl function (R') and the phosphorus atom. The reaction takes place in an inert organic solvent at a temperature between room temperature and about 100° C.

The compounds of formulas I and II where Ar is substituted by carbamyl or carboxy are preferably prepared by reacting the corresponding compounds when Ar is substituted by carbo-lower-alkoxy with ammonia or with an alkaline hydrolysis medium, respectively; although it is possible to effect the functional group conversion prior to the phosphonate alkylation process if desired.

The structures of the compounds of the invention were established by the modes of synthesis, by elementary analysis, and by infrared and nuclear magnetic resonance spectral determinations.

Biological evaluation of the compounds of the invention has shown that they possess antiviral activity. They are thus useful in combatting viruses present on inanimate surfaces as well as viral infections in animal organisms. The in vitro testing of the compounds of the invention against herpes simplex viruses types 1 and 2 and various RNA viruses has showed that they inhibited viral growth at minimum concentrations (MIC) ranging from about 0.4 to about 25 micrograms per milliliter. The MIC values were determined by standard serial dilution procedures. In vivo activity has also been demonstrated in the treatment of mouse genital herpes simplex type 2 infection, and guinea pig herpetic skin infection.

The antiviral compositions are formulated by preparing a dilute solution or suspension in an organic or aqueous-organic medium, for example ethyl alcohol, acetone, dimethyl sulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams. The antivirally effective component of the composition is present in a concentration of between about 0.7 parts per million and about 5 percent by weight, depending upon the chemical species used, the object to be treated and the type of formulation employed. For disinfection of inanimate surfaces with aqueous or aqueous-organic solutions, concentrations in the lower part of the range are effective. For topical application in medical or veterinary use in the form of ointment, cream, jelly or aerosol, concentrations in the upper part of the range are preferred.

The following examples will further illustrate the invention without the latter being limited thereby.

EXAMPLE 1

Diethyl [6-(2-chloro-4-methoxyphenoxy)hexyl]phosphonate [I; Ar is 2-Cl-4-CH$_3$OC$_6$H$_3$, Y is O(CH$_2$)$_6$, R is C$_2$H$_5$]

A mixture of 10 g (0.0313 mole) of 6-(2-chloro-4-methoxyphenoxy)hexyl bromide and 5.2 g (0.313 mole) of triethyl phosphite was heated at 180°–190° C. for two hours. The reaction mixture was distilled in vacuo, and the fraction (4.6 g) collected at 183°–185° C. (0.03 mm) was redistilled to give 3.6 g of diethyl [6-(2-chloro-4-methoxyphenoxy)hexyl]phosphonate, b.p. 195°–197° C. (0.005 mm).

Anal. Calcd. for C$_{17}$H$_{28}$ClO$_5$P: C, 53.90; H, 7.45; Cl, 9.36. Found: C, 53.88; H, 7.51; Cl, 9.71.

EXAMPLE 2

Diethyl [6-(2-chloro-4-methoxyphenoxy)hexyl]phosphonate

Triethyl phosphite (185 g, 230 ml, 1.1 mole) was placed in a flask equipped with a thermometer, dropping funnel, stirrer and 8 inch Vigreux column with condenser set for downward distillation. The phosphite was heated to 158° C. thereby inducing mild reflux. 6-(2-Chloro-4-methoxyphenoxy)hexyl bromide (320 g, 1 mole) was then added dropwise over a period of 50 minutes. The reaction mixture was heated for an additional 90 minutes at which time distillation of ethyl bromide ceased. The remaining reaction mixture was distilled in vacuo and the fraction (250 g) boiling at 183°–197° C. (0.2–0.3 mm) was collected. The latter was combined with 79 g of product obtained from another run starting from 100 g of bromide and redistilled to give 300 g of diethyl [6-(2-chloro-4-methoxyphenoxy)hexyl]phosphonate, b.p. 202°–204° C. (0.02 mm).

Diethyl [6-(2-chloro-4-methoxyphenoxy)hexyl]phosphonate in in vitro tissue culture experiments was found to inhibit either cytopathic effect or plaque formation by 5 strains of herpes simplex virus type 1 or 2. Using a plaque assay, it was established that a 50% plaque inhibition of the herpes viruses was obtained with 3–4 micrograms per ml of this compound. The minimal inhibitory concentration of this compound against para influenza type 3 in cultures of BSC-1 cells was 4 mcg/ml, and for human rhinovirus type 14 in CATR cells it was 6 mcg/ml. A greater than 50% plaque inhibition of poliovirus, Leon strain, in cultures of HeLa cells was obtained with 0.4 mcg/ml of this compound.

Evaluation of diethyl [6-(2-chloro-4-methoxyphenoxy)hexyl]phosphonate against influenza virus in chick embryo trachea organ culture indicated that concentrations of 4 mcg/ml reduced the virus replication of three strains of influenza virus type A2 (Jap 170, Hong Kong and Taiwan) by approximately 99%. The growth of a strain of influenza B (Maryland) was reduced by 95% while two strains of influenza A (PR 8 and Ann Arbor) were reduced by less than 90%. No cytotoxicity of the ciliary cells was observed.

In in vivo testing, topical application of diethyl [6-(2-chloro-4-methoxyphenoxy)hexyl]phosphonate in herpetic skin infection in guinea pigs as an 8% preparation in either vanishing cream or in 90% dimethyl sulfoxide (DMSO) was found to be effective in reducing herpetic vesicles. Five treatments with the DMSO formulation in the course of 24 hours produced immediate and total inhibition of herpetic vesicles without a single relapse in a seven-day observation period.

Diethyl [6-(2-chloro-4-methoxyphenoxy)hexyl]-phosphonate was also evaluated in a mouse genital infection produced by herpes simplex virus type 2. Intravaginal administration of the compound starting 4 hours postinfection either as a 5% or 10% suspension in gum tragacanth applied in saturated cotton tampons produced a survival rate of up to 80% vs. 10% of placebo-treated controls. Similarly, application of 8% of the compound in vanishing cream produced 60% survival rate vs. 0% in placebo-treated controls.

EXAMPLE 3

Dibutyl [6-(2-chloro-4-methoxyphenoxy)hexyl]phosphonate [I; Ar is 2-Cl-4-CH$_3$OC$_6$H$_3$, Y is O(CH$_2$)$_6$, R is (CH$_2$)$_3$CH$_3$]

Sodium metal (0.575 g, 0.025 mole) was placed in 75 ml of hexane, the mixture stirred and heated to gentle reflux, and 4.85 g (0.025 mole) of dibutyl phosphonate was added dropwise over a period of 20 minutes. The mixture was stirred and refluxed until the sodium had completely dissolved (about five hours). There was added 8.01 g (0.025 mole) of 6-(2-chloro-4-methoxyphenoxy)hexyl bromide over a 30 minute period. The reaction mixture was stirred at gentle reflux for 6 hours and then filtered to remove solid material. The filtrate was washed six times with water, the hexane remove in vacuo and the residue distilled in high vacuum to give 7.4 g. of dibutyl [6-(2-chloro-4-methoxyphenoxy)hexyl]phosphonate, b.p. 220°–225° C. (0.005 mm); minimum inhibitory concentration (MIC) against herpes simplex type 2=6 mcg/ml.

Anal. Calcd. for C$_{21}$H$_{36}$ClO$_5$P: C, 57.99; H, 8.34; Cl, 8.15. Found: C, 58.05; H, 8.53; Cl, 8.38.

EXAMPLE 4

Diethyl [6-(4-acetoxyphenyl)hexyl]phosphonate [I; Ar is 4-CH$_3$COOC$_6$H$_4$, Y is (CH$_2$)$_6$, R is C$_2$H$_5$]

A mixture of 32.5 g of 6-(4-hydroxyphenyl)hexyl iodide and 17.76 g. of triethyl phosphite was heated at 180°–182° C. for 3 hours with evolution of ethyl iodide. The resulting product was chromatographed on activated magnesium silicate (Florisil ®) and eluted with the solvent series hexane—ether—methanol. Ether—methanol 40:60 and 20:80 brought out 27 g of material containing diethyl [6-(4-hydroxyphenyl)hexyl]phosphonate which was heated on a steam bath for 5 hours with 250 ml of acetic anhydride in order to esterify the phenolic hydroxy group. The esterification mixture was concentrated in vacuo, the residue (20 g) combined with 6 g of material from another run and distilled in vacuo, collecting the fraction boiling at 182°–202° C. (0.05 mm). The latter was chromatographed on Florisil using the same solvent series as above. Ether—methanol 90:10 brought out 7.0 g of diethyl ]6-(4-acetoxyphenyl)hexyl]phosphonate as a light yellow oil, the NMR spectrum of which was consistent with the assigned structure except for some possible transesterification with methanol; MIC vs. herpes simplex type 2=3 mcg/ml.

Anal. Calcd. for C$_{18}$H$_{29}$O$_5$P: C, 60.65; H, 8.20; P, 8.69. Found: C, 59.56; H, 8.42; P, 9.09.

Alternatively, the 6-(4-hydroxyphenyl)hexyl iodide starting material in Example 4 can be replaced by a molar equivalent amount of 6-(4-acetoxyphenyl)hexyl iodide and the acetylation step eliminated to give the same product.

EXAMPLE 5

Diethyl [8-(2-chloro-4-methoxyphenoxy)octyl]phosphonate

[I; Ar is 2-Cl-4-CH$_3$OC$_6$H$_3$, Y is O(CH$_2$)$_8$, R is C$_2$H$_5$] was prepared from 26.2 g of 8-(2-chloro-4-methoxyphenoxy)octyl bromide, 12.85 g of triethyl phosphite and a crystal of iodine as a catalyst, according to the procedure of Example 1. The product was distilled in vacuo three times to give 5.5 g. of diethyl [8-(2-chloro-4-methoxyphenoxy)octyl]-phosphonate, b.p. 207°–209° C. (0.08 mm); MIC vs. herpes simplex type 2=3 mcg/ml.

Anal. Calcd. for C$_{19}$H$_{32}$ClO$_5$P: C, 56.09; H, 7.93; Cl, 8.71. Found: C, 56.04; H, 7.94; Cl, 8.69.

EXAMPLE 6

Diethyl [7-(2-chloro-4-methoxyphenoxy)heptyl]phosphonate

[I; Ar is 2-Cl-4-CH$_3$OC$_6$H$_3$, Y is O(CH$_2$)$_7$, R is C$_2$H$_5$] was prepared from 7-(2-chloro-4-methoxyphenoxy)-heptyl bromide and triethyl phosphite according to the procedure of Example 1 and obtained as a colorless liquid, b.p. 194°–195° C. (0.03 mm).

Anal. Calcd. for C$_{18}$H$_{30}$ClO$_5$P: C, 55.03; H, 7.70; Cl, 9.02. Found: C, 55.06; H, 7.72; Cl, 8.92.

EXAMPLE 7

Diethyl [6-(2,6-dichlorophenoxy)hexyl]phosphonate

[I; Ar is 2,6-Cl$_2$C$_6$H$_3$, Y is O(CH$_2$)$_6$, R is C$_2$H$_5$] was prepared from 16.3 g of 6-(2,6-dichlorophenoxy)hexyl bromide and 8.3 g of triethyl phosphite according to the procedure of Example 1, and had the b.p. 160°–170° C. (0.07 mm); yield 12.0 g; MIC vs. herpes simplex type 2=12 mcg/ml. The IR and NMR spectra were consistent with the assigned structure.

Anal. Calcd. for C$_{16}$H$_{25}$Cl$_2$O$_4$P: C, 50.12; H, 6.57; Cl, 18.50. Found: C, 50.04; H, 6.52; Cl, 18.87.

EXAMPLE 8

Diethyl [6-(4-carbethoxyphenoxy)hexyl]phosphonate

[I; Ar is 4-C$_2$H$_5$OOCC$_6$H$_4$, Y is O(CH$_2$)$_6$, R is C$_2$H$_5$] was prepared from 15 g of 6-(4-carbethoxyphenoxy)-hexyl bromide, 8.3 g of triethyl phosphite and a crystal of sodium iodide as a catalyst, according to the procedure of Example 1, and had the b.p. 190°–196° C. (0.2 mm); yield 9.5 g; MIC vs. herpes simplex type 2=6 mcg/ml. The IR and NMR spectra were consistent with the assigned structure.

Anal. Calcd. for C$_{19}$H$_{31}$O$_6$P: C, 59.06; H, 8.09; P, 8.02. Found: C, 59.29; H, 8.29; P, 7.87.

EXAMPLE 9

Diethyl 8 6-(4-carboxyphenoxy)hexyl]phosphonate [I; Ar is 4-HOOCC$_6$H$_4$, Y is O(CH$_2$)$_6$, R is C$_2$H$_5$]

A solution (21 ml) of 1N sodium hydroxide in ethanol was added to a solution of 8.3 g of diethyl [6-(4-carbethoxyphenoxy)hexyl]phosphonate (Example 8) in 20 ml of ethanol. The reaction mixture was stirred at room temperature for two days. The solid fraction was collected, digested with 100 ml of ether, filtered and dried to give 7.0 g of diethyl [6-(4-carboxyphenoxy)hexyl]-phosphonate in the form of its sodium salt, m.p. 215°–216° C.

Anal. Calcd. for $C_{17}H_{26}NaO_6P$: C, 62.18; H, 8.90; P, 9.43. Found: C, 61.97; H, 8.79; P, 9.28.

Alternatively, diethyl [6-(4-carboxyphenoxy)-hexyl]-phosphonate can be prepared from 6-(4-carboxyphenoxy)-hexyl bromide and triethyl phosphite in accordance with the procedure of Example 1.

It is further contemplated that diethyl [6-(4-carbethoxyphenoxy)hexyl]phosphonate can be reacted with ammonia in ethanol to give diethyl [6-(4-carbamyl-phenoxy)-hexyl]phosphonate [I; Ar is 4-$H_2NCOC_6H_4$, Y is $O(CH_2)_6$, R is $C_2H_5$].

EXAMPLE 10

Diethyl [6-(4-methoxyphenyl)hexyl]phosphonate

[I; Ar is 4-$CH_3OC_6H_4$, Y is $(CH_2)_6$, R is $C_2H_5$] was prepared from 12.72 g of 6-(4-methoxyphenoxy)hexyl iodide and 6.64 g of triethyl phosphite according to the procedure of Example 1, and had the b.p. 165° C. (0.025 mm); yield 8.2 g; MIC vs. herpes simplex type 2=6 mcg/ml.

Anal. Calcd. for $C_{17}H_{29}O_4P$: C, 62.18; H, 8.90; P, 9.43. Found: C, 61.97; H, 8.79; P, 9.28.

According to the procedures of the preceding examples, it is contemplated that the following intermediates:
6-phenylhexyl iodide
6-(4-fluorophenyl)hexyl iodide
6-phenoxyhexyl bromide
6-(4-bromophenyl)hexyl iodide
6-(4-iodophenyl)hexyl iodide
can be reacted with triethyl phosphite to give, respectively:
Diethyl (6-phenylhexyl)phosphonate [I; Ar is $C_6H_5$, Y is $(CH_2)_6$, R is $C_2H_5$]
Diethyl [6-(4-fluorophenyl)hexyl]phosphonate [I; Ar is 4-$FC_6H_4$, Y is $(CH_2)_6$, R is $C_2H_5$]
Diethyl (6-phenoxyhexyl)phosphonate [I; Ar is $C_6H_5$, Y is $O(CH_2)_6$, R is $C_2H_5$]
Diethyl [6-(4-bromophenyl)hexyl]phosphonate [I; Ar is 4-$BrC_6H_4$, Y is $(CH_2)_6$, R is $C_2H_5$]
Diethyl [6-(4-iodophenyl)hexyl]phosphonate [I; Ar is 4-$IC_6H_4$, Y is $(CH_2)_6$, R is $C_2H_5$].

EXAMPLE 11

Ethyl 8-(2-chloro-4-methoxyphenoxy)-2-(diethoxyphosphinyl)-octanoate [II; Ar is 2-Cl-4-$CH_3OC_6H_3$, Y is $O(CH_2)_6$, R is $C_2H_5$, R' is $C_2H_5OCO$]

Potassium metal (623 mg) was added in small portions to a solution of 3.5 g of triethyl phosphonoacetate in 20 ml of xylene. The mixture was heated at reflux for one hour and then a solution of 5 g of 6-(2-chloro-4-methoxyphenoxy)hexyl bromide in 5 ml of xylene was added. The reaction mixture was refluxed for five hours, then cooled and filtered, and the filtrate concentrated in vacuo. The residue was distilled in vacuo to give 3.7 g of ethyl 8-(2-chloro-4-methoxyphenoxy)-2-(diethoxyphosphinyl)octanoate, b.p. 188°–192° C. (0.04 mm); MIC vs. herpes simplex type 2=3 mcg/ml.

Anal. Calcd. for $C_{21}H_{34}ClO_7P$: C, 54.25; H, 7.37; Cl, 7.63. Found: C, 54.12; H, 7.41; Cl, 7.77.

EXAMPLE 12

(a) Diethyl acetonylphosphonate [$CH_3COCH_2PO(OC_2H_5)_2$]

Iodoacetone (56.5 g., 0.31 mole) was added dropwise over a 20 minute period to 41.4 g (0.31 mole) of triethyl phosphite at 0° C. The mixture was allowed to warm to room temperature and held there for 90 minutes. The crude product was distilled in vacuo and the fraction boiling at 76°–86° C. (0.3–0.35 mm) was collected, giving 12.2 g of diethyl acetonylphosphonate.

(b) Diethyl [1-acetyl-5-(4-methoxyphenyl)pentyl]phosphonate [II; Ar is 4-$CH_3OC_6H_4$, Y is $(CH_2)_4$, R' is $CH_3CO$]

Lithium hydride (0.71 g. 0.09 mole) was added to 90 ml of dry dimethylformamide (DMF) under a nitrogen atmosphere. The mixture was stirred for 10 minutes and there was then added 17.2 g (0.089 mole) of diethyl acetonylphosphonate. The resulting mixture was stirred one hour at 50° C., then cooled and a solution of 25.8 g (0.089 mole) of 4-(4-methoxyphenyl)butyl iodide in 80 ml of DMF was added. The reaction mixture was stirred for 2 days at 40° C., and then concentrated in vacuo at 70° C. The residue was chromatographed on Florisil and eluted with the solvent series hexane—ether—methanol. Ether—methanol 90:10 brought out 12.4 g. of diethyl [1-acetyl-5(4-methoxyphenyl)pentyl]-phosphonate as a yellow oil; MIC vs. herpes simplex type 2=25 mcg/ml. The IR spectrum was consistent with the assigned structure.

Anal. Calcd. for $C_{18}H_{29}O_5P$: C, 60.65; H, 8.20; P, 8.69. Found: C, 60.57; H, 8.23; P, 8.89.

EXAMPLE 13

Diethyl [1-acetyl-8-(2-chloro-4-methoxyphenoxy)octyl]-phosphonate

[II; Ar is 2-Cl-4-$CH_3OC_6H_3$, Y is $O(CH_2)_7$, R is $C_2H_5$, R' is $CH_3CO$] was prepared from 0.57 g of lithium hydride, 13.9 g of diethyl acetonylphosphonate and 27.8 g of 7-(2-chloro-4-methoxyphenoxy)heptyl iodide according to the procedure of Example 12(b). The product was chromatographed on Florisil and further purified by preparative thin layer chromatography (TLC) on silica gel to give 5.9 g of diethyl [1-acetyl-8-(2-chloro-4-methoxyphenoxy)octyl]phosphonate as a yellow oil; MIC vs. herpes simplex type 2=6 mcg/ml. The NMR spectrum was consistent with the assigned structure.

Anal. Calcd. for $C_{21}H_{34}ClO_6P$: C, 56.18; H, 7.63; P, 6.58. Found: C, 56.06; H, 7.73; P, 6.72.

EXAMPLE 14

Diethyl [1-acetyl-9-(2-chloro-4-methoxyphenoxy)nonyl]-phosphonate

[II; Ar is 2-Cl-4-$CH_3OC_6H_3$, Y is $O(CH_2)_8$, R is $C_2H_5$, R' is $CH_3CO$] was prepared from 0.38 g of lithium hydride, 9.5 g of diethyl acetonylphosphonate and 19.4 g of 8-(2-chloro-4-methoxyphenoxy)octyl iodide according to the procedure of Example 12(b). The product was chromatographed on Florisil to give 5.67 g of diethyl [1-acetyl-9-(2-chloro-4-methoxyphenoxy)-nonyl]phosphonate as a light yellow oil; MIC vs. herpes simplex type 2=12 mcg/ml. The NMR spectrum was consistent with the assigned structure.

Anal. Calcd. for $C_{22}H_{36}ClO_6P$: C, 57.07; H, 7.83; P, 6.69. Found: C, 57.37; H, 7.90; P, 6.81.

EXAMPLE 15

Diethyl [1-acetyl-6-(2-chloro-4-methoxyphenoxy)hexyl]-phosphonate

[II; Ar is 2-Cl-4-CH$_3$OC$_6$H$_3$, Y is O(CH$_2$)$_5$, R is C$_2$H$_5$, R' is CH$_3$CO] was prepared from 0.71 g of lithium hydride, 17.2 g of diethyl acetonylphosphonate and 34 g of 5-(2-chloro-4-methoxyphenoxy)pentyl iodide according to the procedure of Example 12(b). The product was chromatographed on Florisil and further purified by preparative TLC on silica gel to give 6.3 g of diethyl [1-acetyl-6(2-chloro-4-methoxyphenoxy)hexyl]phosphonate as a light yellow oil; MIC vs. herpes simplex type 2=6 mcg/ml. The IR spectrum was consistent with the assigned structure.

Anal. Calcd. for $C_{19}H_{30}ClO_6P$: C, 54.21; H, 7.18; P, 7.36. Found: C, 54.09; H, 7.15; P, 7.49.

EXAMPLE 16

Diethyl [1-acetyl-5-(2-chloro-4-methoxyphenoxy)pentyl]-phosphonate

[II; Ar is 2-Cl-4-CH$_3$OC$_6$H$_3$, Y is O(CH$_2$)$_4$, R is C$_2$H$_5$, R' is CH$_3$CO] was prepared from 0.79 g of lithium hydride, 19.4 g of diethyl acetonylphosphonate and 34.0 g of 4-(2-chloro-4-methoxyphenoxy)butyl iodide according to the procedure of Example 12(b). The product was chromatographed on Florisil to give 6.45 g of diethyl [1-acetyl-5-(2-chloro-4-methoxyphenoxy)-pentyl]phosphonate as a yellow oil; MIC vs. herpes simplex type 2=12 mcg/ml. The NMR spectrum was consistent with the assigned structure.

Anal. Calcd. for $C_{18}H_{28}ClO_6P$: C, 53.14; H, 6.93; Cl, 8.71. Found: C, 53.30; H, 6.98; Cl, 8.70.

EXAMPLE 17

Diethyl [1-acetyl-7-(2-chloro-4-methoxyphenoxy)heptyl]-phosphonate [II; Ar is 2-Cl-4-CH$_3$OC$_6$H$_3$, Y is O(CH$_2$)$_6$, R is C$_2$H$_5$, R' is CH$_3$CO] was prepared from 0.47 g of lithium hydride, 11.6 g of diethyl acetonylphosphonate and 22 g of 6-(2-chloro-4-methoxyphenoxy)hexyl iodide according to the procedure of Example 12(b). The product was chromatographed on Florisil and further purified by preparative TLC on silica gel to give 5.0 g of diethyl [1-acetyl-7-(2-chloro-4-methoxyphenoxy)heptyl]phosphonate as a yellow oil; MIC vs. herpes simplex type 2=6 mcg/ml. The IR and NMR spectra were consistent with the assigned structure.

Anal. Calcd. for $C_{20}H_{32}ClO_6P$: C, 55.23; H, 7.92. Found: C, 54.91; H, 7.30.

According to the procedures of Examples 11–17, it is contemplated that the following intermediates:

6-phenylhexyl iodide
6-(4-fluorophenyl)hexyl iodide
6-phenoxyhexyl bromide
6-(4-bromophenyl)hexyl iodide
6-(4-iodophenyl)hexyl iodide
6-(4-hydroxyphenyl)hexyl iodide
6-(4-acetoxyphenyl)hexyl iodide
6-(4-carbethoxyphenoxy)hexyl bromide can be caused to react with diethyl acetonylphosphonate to give, respectively:

Diethyl (1-acetyl-7-phenylheptyl)phosphonate [II; Ar is C$_6$H$_5$, Y is (CH$_2$)$_6$, R is C$_2$H$_5$, R' is CH$_3$CO]

Diethyl [1-acetyl-7-(4-fluorophenyl)heptyl]phosphonate [II; Ar is 4-FC$_6$H$_4$, Y is (CH$_2$)$_6$, R is C$_2$H$_5$, R' is CH$_3$CO]

Diethyl (1-acetyl-7-phenoxyheptyl)phosphonate [II; Ar is C$_6$H$_5$, Y is O(CH$_2$)$_6$, R is C$_2$H$_5$, R' is CH$_3$CO]

Diethyl [1-acetyl-7-(4-bromophenyl)heptyl]phosphonate [II; Ar is 4-BrC$_6$H$_4$, Y is (CH$_2$)$_6$, R is C$_2$H$_5$, R' is CH$_3$CO]

Diethyl [1-acetyl-7-(4-iodophenyl)heptyl]phosphonate [II; Ar is 4-IC$_6$H$_4$, Y is (CH$_2$)$_6$, R is C$_2$H$_5$, R' is CH$_3$CO]

Diethyl [1-acetyl-7-(4-hydroxyphenyl)heptyl]phosphonate [II; Ar is 4-HOC$_6$H$_4$, Y is (CH$_2$)$_6$, R is C$_2$H$_5$, R' is CH$_3$CO]

Diethyl [1-acetyl-7-(4-acetoxyphenyl)heptyl]phosphonate [II; Ar is 4-CH$_2$COOC$_6$H$_4$, Y is (CH$_2$)$_6$, R is C$_2$H$_5$, R' is CH$_3$CO]

Diethyl [1-acetyl-7-(4-carbethoxyphenoxy)heptyl]-phosphonate [II; Ar is 4-C$_2$H$_5$OOCC$_6$H$_4$, Y is O(CH$_2$)$_6$, R is C$_2$H$_5$, R' is CH$_3$CO].

The last named compound can be hydrolyzed with sodium hydroxide in ethanol (see Example 9 for procedure) to give diethyl [1-acetyl-7-(4-carboxyphenoxy)-heptyl]-phosphonate [II; Ar is 4-HOOCC$_6$H$_4$, Y is O(CH$_2$)$_6$, R is C$_2$H$_5$, R' is CH$_3$CO].

It is further contemplated that diethyl [1-acetyl-7-(4-carbethoxyphenoxy)heptyl]phosphonate can be reacted with ammonia in ethanol to give diethyl [1-acetyl-7-(4-carbamylphenoxy)heptyl]phosphonate [II; Ar is 4-H$_2$NCOC$_6$H$_4$, Y is O(CH$_2$)$_6$, R is C$_2$H$_5$, R' is CH$_3$CO].

I claim:

1. A compound having the formula

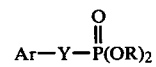

wherein

Ar is phenyl or phenyl substituted by one or two substituents selected from the group consisting of halogen, lower-alkoxy of 1 to 4 carbon atoms, hydroxy, alkanoyloxy of 1–4 carbon atoms, carbo-lower-alkoxy of 2–4 carbon atoms, carbamyl and carboxy;

Y is (CH$_2$)$_n$ or O(CH$_2$)$_n$ wherein n is an integer from 6 to 8;

and R is alkyl of 1–6 carbon atoms.

2. A method for combatting viruses which comprises contacting the locus of said viruses with an antivirally effective amount of at least one compound according to claim 1.

3. A method according to claim 2 wherein the antivirally effective compound is diethyl [6-(2-chloro-4-methoxyphenoxy)hexyl]phosphonate.

4. A composition for combatting viruses which comprises an antivirally effective amount of at least one compound according to claim 1 in admixture with a suitable carrier or diluent.

5. A composition according to claim 4 wherein the antivirally effective compound is diethyl [6-(2-chloro-4-methoxyphenoxy)hexyl]phosphonate.

6. A compound according to claim 1 wherein Y is O(CH$_2$)$_6$.

7. A compound according to claim 1 wherein Ar is 2-chloro-4-methoxyphenyl and Y is O(CH$_2$)$_6$.

8. Diethyl [6-(2-chloro-4-methoxyphenoxy)hexyl]-phosphonate, according to claim 7.

9. Dibutyl [6-(2-chloro-4-methoxyphenoxy)hexyl]-phosphonate, according to claim 7.

10. Diethyl [6-(4-acetoxyphenyl)hexyl]phosphonate, according to claim 6.

11. Diethyl [6-(2,6-dichlorophenoxy)hexyl]-phosphonate, according to claim 6.

12. Diethyl [6-(4-carbethoxyphenoxy)hexyl]-phosphonate, according to claim 6.

13. Diethyl [6-(4-methoxyphenyl)hexyl]phosphonate, according to claim 6.

14. Diethyl [6-(4-carboxyphenoxy)hexyl]phosphonate, according to claim 6.

15. Diethyl [8-(2-chloro-4-methoxyphenoxy)octyl]-phosphonate, according to claim 1.

* * * * *

UNITED STATES PATENT AND TRADEMARK OFFICE
CERTIFICATE OF CORRECTION

PATENT NO. : 4,182,759
DATED : January 8, 1980
INVENTOR(S) : Guy D. Diana

It is certified that error appears in the above-identified patent and that said Letters Patent are hereby corrected as shown below:

Cover page, OTHER PUBLICATIONS, "vol. 10, (1970)" should read --vol. 10, (1975)--.

Column 2, line 63, "arylakyl" should read --arylalkyl--.

Column 3, line 7, "arylakyl" should read --arylalkyl--.

Column 5, line 35, "remove" should read --removed--.

Column 6, line 63, "8 6-" should read --[6- --.

Column 8, line 15, after "$(CH_2)_4$," insert --R is $C_2H_5$,--.

Column 10, line 21, "$4-CH_2COOC_6H_4$" should read --$4-CH_3COOC_6H_4$--.

Signed and Sealed this

Third Day of June 1980

[SEAL]

Attest:

SIDNEY A. DIAMOND

*Attesting Officer*  *Commissioner of Patents and Trademarks*

REEXAMINATION CERTIFICATE (285th)
United States Patent [19]
Diana

[11] B1 4,182,759
[45] Certificate Issued  Dec. 18, 1984

[54] ARYLALKYL AND ARYLOXYALKYL PHOSPHONATES AND USE AS ANTIVIRAL AGENTS

[75] Inventor: Guy D. Diana, Stephentown, N.Y.

[73] Assignee: Sterling Drug Inc., New York, N.Y.

Reexamination Request:
No. 90/000,546, Apr. 18, 1984

Reexamination Certificate for:
Patent No.: 4,182,759
Issued: Jan. 8, 1980
Appl. No.: 912,502
Filed: Jun. 5, 1978

[51] Int. Cl.$^3$ .................. A01N 9/36; C07F 9/40
[52] U.S. Cl. .................. 424/217; 260/941; 260/943; 260/951; 260/952; 260/961; 424/211; 424/212; 424/222
[58] Field of Search .............. 424/211, 212, 217, 222; 260/941, 943, 951, 952, 961, 946

[56] References Cited
U.S. PATENT DOCUMENTS

| | | | |
|---|---|---|---|
| 2,934,507 | 4/1960 | Chadwick et al. | 260/951 |
| 3,134,800 | 5/1964 | Kagan et al. | 260/456 |
| 3,917,718 | 11/1975 | Collins | 260/613 R |
| 4,031,246 | 6/1977 | Collins et al. | 424/331 |

OTHER PUBLICATIONS

Papukova et al., Journal of Applied Chemistry of the USSR, v. 45 (8):1885–1889, (1972).

*Primary Examiner*—Anton H. Sutto

[57] ABSTRACT

Arylalkyl and aryloxyalkylphosphonates, useful as antiviral agents, are prepared by reacting an arylalkyl or aryloxyalkyl halide with a trialkyl phosphite, or with an alkali metal salt of a dialkyl phosphonate, trialkyl phosphonoalkanoate or dialkyl phosphonoalkanone.

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 61–68 and Column 2, lines 1–27:
In a composition of matter aspect, the invention relates to compounds having the formula

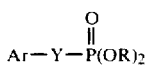

wherein
Ar is [phenyl or] phenyl substituted by one or two substituents selected from the group consisting of halogen, lower-alkoxy of 1 to 4 carbon atoms, hydroxy, alkanoyloxy of 1-4 carbon atoms, carbo-lower-alkoxy of 2-4 carbon atoms, carbamyl and carboxy;
Y is $(CH_2)_n$ or $O(CH_2)_n$ wherein n is an integer from 6 to 8; and R is alkyl of 1-6 carbon atoms.
In a further composition of matter aspect, the invention relates to compounds having the formula

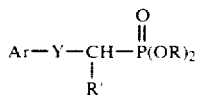

wherein
Ar is [phenyl or] phenyl substituted by one or two substituents selected from the group consisting of halogen, lower-alkoxy of 1 to 4 carbon atoms, hydroxy, alkanoyloxy of 1-4 carbon atoms, carbo-lower-alkoxy of 2-4 carbon atoms, carbamyl and carboxy;
Y is $(CH_2)_m$ or $O(CH_2)_m$ where m is an integer from 3 to 10;
R is alkyl of 1-6 carbon atoms;
and R' is alkanoyl or carboalkoxy of from 2 to 4 carbon atoms.

Column 7, lines 29–48:
According to the procedures of the preceding examples, it is contemplated that the following intermediates:
[6-phenylhexyl iodide]
6-(4-fluorophenyl)hexyl iodide
[6-phenoxyhexyl bromide]
6-(4-bromophenyl)hexyl iodide
6-(4-iodophenyl)hexyl iodide
can be reacted with triethyl phosphite to give, respectively:
[Diethyl (6-phenylhexyl)phosphonate [I; Ar is $C_6H_5$, Y is $(CH_2)_6$, R is $C_2H_5$]]
Diethyl [6-(4-fluorophenyl)hexyl]phosphonate [I; Ar is 4-$FC_6H_4$, Y is $(CH_2)_6$, R is $C_2H_5$]
[Diethyl (6-phenoxyhexyl)phosphonate [I; Ar is $C_6H_5$, Y is $O(CH_2)_6$, R is $C_2H_5$]]
Diethyl [6-(4-bromophenyl)hexyl]phosphonate [I; Ar is 4-$BrC_6H_4$, Y is $(CH_2)_6$, R is $C_2H_5$]
Diethyl [6-(4-iodophenyl)hexyl]phosphonate [I; Ar is 4-$IC_6H_4$, Y is $(CH_2)_6$, R is $C_2H_5$].

Column 9, lines 60–68 and Column 10, lines 1–25:
According to the procedures of Examples 11–17, it is contemplated that the following intermediates:
[6-phenylhexyl iodide]
6-(4-fluorophenyl)hexyl iodide
[6-phenoxyhexyl bromide]
6-(4-bromophenyl)hexyl iodide
6-(4-iodophenyl)hexyl iodide
6-(4-hydroxyphenyl)hexyl iodide
6-(4-acetoxyphenyl)hexyl iodide
6-(4-carbethoxyphenoxy)hexyl bromide
can be caused to react with diethyl acetonylphosphonate to give, respectively:
[Diethyl (1-acetyl-7-phenylheptyl)phosphonate [II; Ar is $C_6H_5$, Y is $(CH_2)_6$, R is $C_2H_5$, R' is $CH_3CO$]]
Diethyl [1-acetyl-7-(4-fluorophenyl)heptyl]phosphonate [II; Ar is 4-$FC_6H_4$, Y is $(CH_2)_6$, R is $C_2H_5$, R' is $CH_3CO$]
[Diethyl (1-acetyl-7-phenoxyheptyl)phosphonate [II; Ar is $C_6H_5$, Y is $O(CH_2)_6$, R is $C_2H_5$, R' is $CH_3CO$]]
Diethyl [1-acetyl-7-(4-bromophenyl)heptyl]phosphonate [II; Ar is 4-$BrC_6H_4$, Y is $(CH_2)_6$, R is $C_2H_5$, R' is $CH_3CO$]
Diethyl [1-acetyl-7-(4-iodophenyl)heptyl]phosphonate [II; Ar is 4-$IC_6H_4$, Y is $(CH_2)_6$, R is $C_2H_5$, R' is $CH_3CO$]
Diethyl [1-acetyl-7-(4-hydroxyphenyl)heptyl]phosphonate [II; Ar is 4-$HOC_6H_4$, Y is $(CH_2)_6$, R is $C_2H_5$, R' is $CH_3CO$]
Diethyl [1-acetyl-7-(4-acetoxyphenyl)heptyl]phosphonate [II; Ar is 4-$CH_2COOC_6H_4$, Y is $(CH_2)_6$, R is $C_2H_5$, R' is $CH_3CO$]
Diethyl [1-acetyl-7-(4-carbethoxyphenoxy)heptyl]phosphonate [II; Ar is 4-$C_2H_5OOCC_6H_4$, Y is $O(CH_2)_6$, R is $C_2H_5$, R' is $CH_3CO$].

AS A RESULT OF REEXAMINATION, IT HAS BEEN DETERMINED THAT:

The patentability of claims 2–15 is confirmed.

Claim 1 is determined to be patentable as amended.

1. A compound having the formula

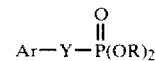

wherein
Ar is [phenyl or] phenyl substituted by one or two substituents selected from the group consisting of halogen, lower-alkoxy of 1 to 4 carbon atoms, hydroxy, alkanoyloxy of 1-4 carbon atoms, carbo-lower-alkoxy of 2-4 carbon atoms, carbamyl and carboxy;
Y is $(CH_2)_n$ or $O(CH_2)_n$ wherein n is an integer from 6 to 8;
and R is alkyl of 1-6 carbon atoms.

* * * * *